United States Patent [19]

Hoffmann

[11] 4,294,762
[45] Oct. 13, 1981

[54] PREPARATION OF α-CYANO-BENZYL ESTERS

[75] Inventor: Hellmut Hoffmann, Wuppertal, Fed. Rep. of Germany

[73] Assignee: Bayer Aktiengesellschaft, Leverkusen, Fed. Rep. of Germany

[21] Appl. No.: 145,636

[22] Filed: May 1, 1980

[30] Foreign Application Priority Data

May 26, 1979 [DE] Fed. Rep. of Germany ....... 2916224

[51] Int. Cl.³ .................. C07C 121/66; C07C 121/75; C07D 317/60; C07D 319/20
[52] U.S. Cl. .......................... 260/340.3; 260/340.5 R; 260/465 D; 260/937; 260/940
[58] Field of Search ................ 260/465 D, 940, 340.3, 260/340.5 R

[56] References Cited

FOREIGN PATENT DOCUMENTS 2281918 3/1976 France .
2393789 1/1979 France .

OTHER PUBLICATIONS

Streitwieser, Jr. et al., "Organische Chemie," 1980 Verlag Chemie, Weinheim, pp. 598–602.

*Primary Examiner*—Dolph H. Torrence
*Attorney, Agent, or Firm*—Sprung, Felfe, Horn, Lynch & Kramer

[57] ABSTRACT

A process for the preparation of an insecticidally active compound such as

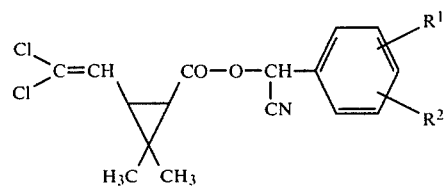

comprising reacting a benzoyl-phosphonic acid ester of the formula

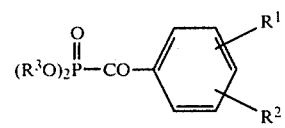

with an alkali metal cyanide in aqueous acetic acid to produce the new compound

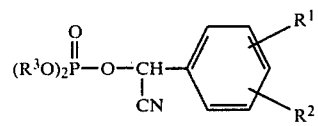

which is reacted with an alkali or alkline earth metal salt of the formula

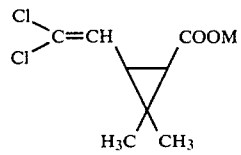

9 Claims, No Drawings

PREPARATION OF α-CYANO-BENZYL ESTERS

The invention relates to an unobvious process for the preparation of certain known α-cyano-benzyl esters, which can be used as arthropodicides.

It is known that certain α-cyano-benzyl esters, for example 3-(2,2-dichlorovinyl)-2,2-dimethyl-cyclopropane-1-carboxylic acid α-cyano-3-phenoxy-benzyl ester, are obtained by reacting reactive carboxylic acid derivatives, for example 3-(2,2-dichlorovinyl)-2,2-dimethyl-cyclopropane-1-carboxylic acid chloride, with α-cyano-benzyl alcohols, for example α-cyano-3-phenoxy-benzyl alcohol (see DE-OS (German Published Specification) No. 2,326,077).

However, in many cases the α-cyano-benzyl alcohols which are required as starting substances for this reaction and which are usually prepared by reacting corresponding benzaldehydes, for example 3-phenoxybenzaldehyde, with alkali metal cyanides, for example potassium cyanide, in the presence of an aqueous acid, for example hydrochloric acid, can be isolated in the pure form and at the same time in good yield only with difficulty.

There are as yet no particularly suitable preparative processes for preparing various substituted benzaldehydes, which are of interest as precursors for pyrethroids having a high insecticidal action, on an industrial scale.

There is thus an interest in processes by which α-cyano-benzyl esters can be prepared without using α-cyano-benzyl alcohols and/or corresponding benzaldehydes.

The present invention now provides:

(1) a process for the preparation of an α-cyano-benzyl ester of the general formula

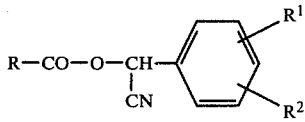

in which
  R represents an open-chain or cyclic alkyl radical which optionally carries one or more substituents selected from halogen, alkyl, cycloalkyl, alkenyl (which is optionally substituted by halogen), styryl (which is optionally substituted by halogen), phenyl (which is optionally substituted by halogen, alkyl, alkoxy, alkylthio, halogenoalkyl, halogenoalkoxy, halogenoalkylthio or optionally halogen-substituted alkylendioxy) and cycloalk(en)yl which is linked in a spirocyclic manner and is optionally benzo-fused,
  $R^1$ represents hydrogen, halogen or an optionally halogen-substituted alkyl, alkenyl, alkynyl, alkoxy, alkenoxy, alkynoxy, aralkyl or aryloxy radical and
  $R^2$ represents hydrogen or halogen,
characterized in that a phosphoric acid α-cyano-benzyl ester of the general formula

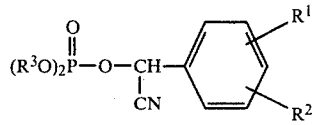

in which
  $R^1$ and $R^2$ have the meanings indicated above and
  $R^3$ represents alkyl, phenyl or alkanediyl (alkylene), is reacted with a carboxylic acid salt of the general formula

in which
  R has the meaning indicated above and
  M represents one equivalent of an alkali metal or alkaline earth metal,
if appropriate using a diluent, at a temperature of about 20° to 250° C.; (2), as new compounds, the phosphoric acid α-cyano-benzyl esters of the general formula

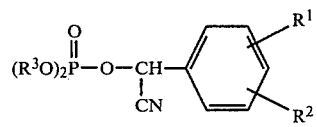

in which
  $R^1$, $R^2$ and $R^3$ have the meanings indicated above; and
(3) a process for the preparation of a phosphoric acid α-cyano-benzyl ester of the formula (II) above, characterized in that a benzoyl-phosphonic acid ester of the general formula

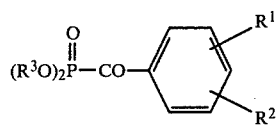

in which
  $R^1$, $R^2$ and $R^3$ have the meanings indicated above, is reacted with an alkali metal cyanide in aqueous acetic acid at a temperature from about −20° to +100° C.

It is surprising that the known carboxylic acid α-cyanobenzyl esters (I) are obtained in a relatively simple manner and in good yields by the new process (1) by reacting carboxylic acid salts (III) with phosphoric acid α-cyano-benzyl esters (II), since according to experience, carboxylic acid salts are to be rated as relatively inert compounds and phosphoric acid α-cyano-benzyl esters are not known to be particularly reactive benzylating agents.

A particular advantage of the new process (1) is that the expensive preparation of α-cyano-benzyl alcohols and/or corresponding aldehydes as intermediate products for carboxylic acid α-cyano-benzyl esters is avoided.

If, for example, the lithium salt of 3-(2,2-dichlorovinyl)-2,2-dimethyl-cyclopropane-1-carboxylic acid and 2-oxo-2-(4-fluoro-3-phenoxy-α-cyano-benzyloxy)-5,5-dimethyl-1,3,2-dioxa-phosphorinane are used as starting materials in process (1), the course of the reaction can be outlined by the following equation:

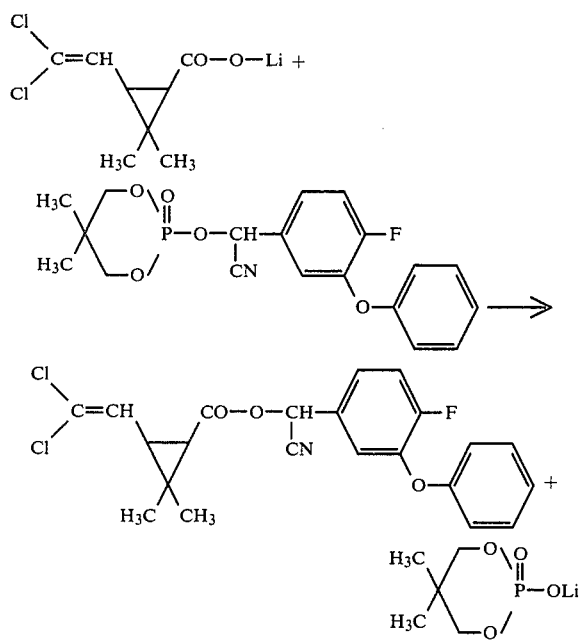

Formula (II) provides a definition of the new phosphoric acid α-cyano-benzyl esters to be used as starting materials. Preferably, in this formula, $R^1$ represents hydrogen or phenoxy which is optionally substituted by fluorine, chlorine or bromine, $R^2$ represents hydrogen, fluorine, chlorine or bromine and $R^3$ represents 2,2-dimethyl-propane-1,3-diyl.

Examples of the compounds of the formula (II) which may be mentioned are: 2-oxo-2-(α-cyano-benzyloxy)-5,5-dimethyl-1,3,2-dioxa-phosphorinane, 2-oxo-2-(3-phenoxy-α-cyano-benzyloxy)-5,5-dimethyl-1,3,2-dioxa-phosphorinane, 2-oxo-2-(3-(4-fluoro-phenoxy)-α-cyano-benzyloxy)-5,5-dimethyl-1,3,2-dioxa-phosphorinane and 2-oxo-2-(4-fluoro-3-phenoxy-α-cyano-benzyloxy)-5,5-dimethyl-1,3,2-dioxa-phosphorinane.

The phosphoric acid α-cyano-benzyl esters are obtained by the process indicated under (3), by reacting benzoylphosphonic acid esters of the formula (IV) above with alkali metal cyanides, preferably with sodium cyanide or potassium cyanide, in aqueous acetic acid at temperatures between −20° and 100° C., preferably about 0° to 50° C.

In a preferred embodiment of this process, the benzoylphosphonic acid ester is initially introduced into acetic acid and an aqueous cyanide solution is added dropwise to this mixture, while cooling with ice-water. After prolonged stirring at room temperature, the mixture is diluted with water. The product thereby obtained in the form of crystals can be isolated by filtration.

In formula (IV), $R^1$ $R^2$ and $R^3$ have the same preferred meanings as the corresponding radicals in formula (II).

Examples which may be mentioned are: 2-oxo-2-benzoyl-5,5-dimethyl-1,3,2-dioxa-phosphorinane, 2-oxo-2-(3-phenoxybenzoyl)-5,5-dimethyl-1,3,2-dioxa-phosphorinane, 2-oxo-2-(3-(4-fluoro-phenoxy)-benzoyl)-5,5-dimethyl-1,3,2-dioxaphosphorinane and 2-oxo-2-(4-fluoro-3-phenoxy-benzoyl)-5,5-dimethyl-1,3,2-dioxa-phosphorinane.

Benzoyl-phosphonic acid esters of the formula (IV) are known (see Houben-Weyl, Methoden der Organischen Chemie (Methods of Organic Chemistry), 4th edition, Volume 12/1, page 453, Georg-Thieme-Verlag, Stuttgart 1963).

Benzoyl-phosphonic acid esters of the formula (IV) are obtained by reacting phosphorous acid esters of the general formula $$(R^3O)_2P-OR^3 \quad (V),$$

in which $R^3$ has the meaning indicated above and $R^4$ represents methyl or ethyl, with benzoyl halides of the general formula

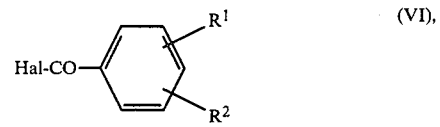

in which $R^1$ and $R^2$ have the meanings indicated above and

Hal represents fluorine, chlorine or bromine, preferably chlorine, if appropriate in the presence of an acid-binding agent and if appropriate using a diluent, at a temperature between about 0° and 150° C., preferably between about 20° and 100° C.

In the formulae (V) and (VI), $R^1$, $R^2$ and $R^3$ have the same preferred meanings as in formula (I).

An example of the phosphorous acid esters of the formula (V) which may be mentioned is 2-ethoxy-5,5-dimethyl-1,3,2-dioxa-phosphorinane. This compound is already known (see Chem. Abstracts 85 (1976), 21 557g).

Examples of the benzoyl halides of the formula (VI) which may be mentioned are: benzoyl chloride, 3-phenoxybenzoyl chloride, 3-(4-fluorophenoxy)-benzoyl chloride and 4-fluoro-3-phenoxy-benzoyl chloride.

Compounds of the formula (VI) are already known (see British Pat. No. 1,052,390).

Formula (III) provides a definition of the carboxylic acid salts also to be used as starting materials. Preferably, in this formula, R represents a radical of the general formula

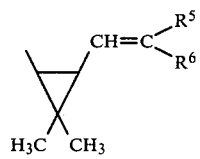

wherein $R^5$ represents hydrogen, methyl, chlorine or bromine and $R^6$ represents methyl, chlorine, bromine or optionally halogen-substituted phenyl, or R represents the radical

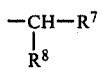

wherein
R[7] represents phenyl which is optionally substituted by halogen, $C_1$–$C_4$-alkyl, $C_1$–$C_4$ alkoxy, $C_1$–$C_4$-alkylthio, halogenomethyl, $C_1$–$C_2$-halogenoalkoxy, $C_1$–$C_2$-halogenoalkylthio, $C_1$–$C_2$-alkylenedioxy or $C_1$–$C_2$-halogenoalkylenedioxy and
R[8] represents isopropyl or cyclopropyl.

M in formula (III) represents lithium, sodium or potassium, for preference.

Examples of the compounds of the formula (III) which may be mentioned are: the lithium, sodium and potassium salts of 3-(2,2-dichloro-vinyl)-2,2-dimethyl-cyclopropane-1-carboxylic acid, 3-(2,2-dibromo-vinyl)-2,2-dimethylcyclopropane-1-carboxylic acid, 3-(2-methyl-propen-1-yl)-2,2-dimethyl-cyclopropane-1-carboxylic acid, 3-(2-phenyl-vinyl)-2,2-dimethyl-cyclopropane-1-carboxylic acid, 3-(2-(4-chloro-phenyl)-vinyl)-2,2-dimethyl-cyclopropane-1-carboxylic acid, 3-(2-chloro-2-phenyl-vinyl)-2,2-dimethylcyclopropane-1-carboxylic acid, 3-(2-chloro-2-(4-chlorophenyl)-vinyl)-2,2-dimethyl-cyclopropane-1-carboxylic acid, α-isopropyl-phenylacetic acid, α-isopropyl-4-chloro-phenylacetic acid, α-isopropyl-4-methyl-phenyl-acetic acid, α-isopropyl-4-methoxy-phenyl-acetic acid, α-isopropyl-4-trifluoromethoxy-phenyl-acetic acid, α-isopropyl-3,4-methylenedioxy-phenyl-acetic acid, α-cyclopropyl-phenyl-acetic acid and α-cyclopropyl-4-chloro-phenyl-acetic acid.

Carboxylic acid salts of the formula (III) and the corresponding acids or esters from which the salts can be prepared by reaction with alkali metal hydroxides or alcoholates are known (see DE-OS's (German Published Specifications) Nos. 1,926,433, 2,365,555, 2,544,150 and 2,730,515).

The process (1) according to the invention for the preparation of α-cyano-benzyl esters is preferably carried out using an aprotic dipolar diluent. Preferred diluents which may be mentioned are: ethers, for example glycol dimethyl ether, diglycol dimethyl ether, tetrahydrofuran and dioxane; carboxylic acid amides, for examples dimethylformamide, dimethylacetamide and N-methylpyrrolidone; sulphoxides and sulphones, for example dimethylsulphoxide and tetramethylene sulphone; phosphoric acid amides, for example hexamethylphosphoric acid triamide; and nitriles, for example acetonitrile and propionitrile.

The reaction temperature is in general from 20° to 250° C., preferably about 100° to 200° C., in process (1) according to the invention. The reaction is in general carried out under normal pressure or under a pressure matching the vapor pressure of the diluent at the particular reaction temperature.

For carrying out process (1), in general from 0.8 to 1.5 moles, preferably about 1.0 to 1.3 moles, of carboxylic acid salt (III) are employed per mole of phosphoric acid α-cyano-benzyl ester (II). The reactants are mixed at room temperature, in one of the diluents indicated; the reaction mixture is then heated to the required reaction temperature and stirred at this temperature for several hours.

Working up is effected by customary methods: after cooling, the mixture is poured into water and the product is extracted with a water-immiscible solvent, for example ligroin, or a mixture of such solvents. The extraction solution is washed with water and dried. The solvent is removed by distillation under reduced pressure and, if appropriate, the crude product which remains is purified by distillation.

Some of the products cannot be distilled without decomposition; however, then can be freed from volatile constituents by so-called "incipient distillation," that is to say by prolonged heating to moderately elevated temperatures under reduced pressure, and purified in this manner. The products are characterized by their refractive index.

α-Cyano-benzyl esters of the formula (I) to be prepared by the process according to the invention are known. They are used as arthropodicides, in particular as insecticides and acaricides (see DE-OS's (German Published Specifications) Nos. 2,326,077 and 2,730,515).

The active compounds are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The above-mentioned pests include:

from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia; from the order of the Isoptera, for example Reticulitermes spp.;* from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubi-*

*lalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylenefatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.0001 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The present invention also provides an arthropodicidal composition containing as active ingredient a compound of the present invention in admixture with a solid or liquefied gaseous diluent or carrier or in admixture with a liquid diluent or carrier containing a surfaceactive agent.

The present invention also provides a method of combating arthropods (especially insects or acarids) which comprises applying to the arthropods, or to a habitat thereof, a compound of the present invention alone or in the form of a composition containing as active ingredient a compound of the present invention in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

Preparation of the starting compounds

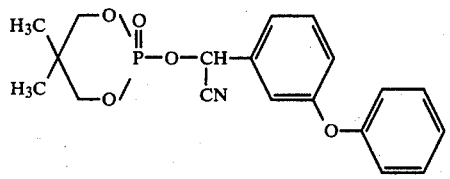

A solution of 28 g of potassium cyanide in 50 ml of water was added dropwise to a solution of 70 g of 2-oxo-2-(3-phenoxybenzoyl)-5,5-dimethyl-1,3,2-dioxa-phosphorinane in 180 ml of glacial acetic acid at approximately 20° C. in the course of one hour, while cooling with ice-water. The reaction mixture was stirred at 20° C. for about 20 hours, 800 ml of water were added, while stirring intensively, and the mixture was stirred for three hours.

The product, which was obtained in the solid form, was isolated by filtration and dried. For purification, it was made into a slurry with a mixture of 150 ml of methanol and 150 ml of water, filtered off and dried on clay. 48 g (64% of theory) of 2-oxo-2-(3-phenoxy-α-cyano-benzyloxy)-5,5-dimethyl-1,3,2-dioxa-phosphorinane with a melting point of 140° C. were obtained.

The following compounds were obtained analogously:

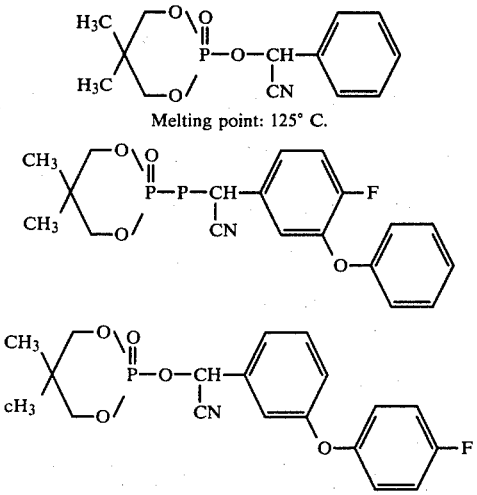

Preparation of the precursors

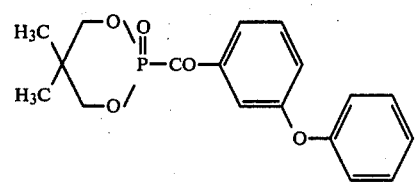

18 g of 2-ethoxy-5,5-dimethyl-1,3,2-dioxaphosphorinane were added dropwise to 23.5 g of 3-phenoxybenzoyl chloride at 60°–70° C., with exclusion of air. The reaction mixture was stirred at 80° C. for one hour and the ethyl chloride formed as a by-product was then stripped off under a high vacuum.

30 g (87% of theory) of 2-oxo-2-(3-phenoxybenzoyl)-5,5-dimethyl-1,3,2-dioxa-phosphorinane were obtained.

The following compounds were obtained analogously:

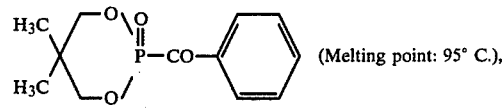 (Melting point: 95° C.),

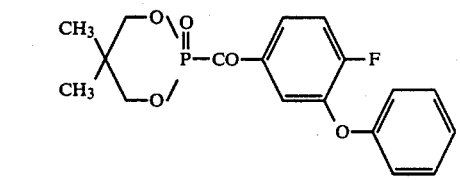

and

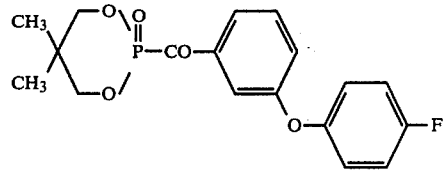

Preparation of the end products

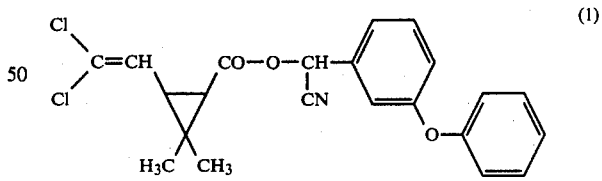 (1)

A slurry of 38 g of 2-oxo-2-(3-phenoxy-α-cyanobenzyloxy)-5,5-dimethyl-1,3,2-dioxa-phosphorinane, 26 g of the sodium salt of 3-(2,2-dichloro-vinyl)-2,2-dimethylcyclopropane-1-carboxylic acid and 260 g of diglycol dimethyl ether was heated to 150° C. for 20 hours, while stirring. After cooling, the mixture was poured into water and the product was extracted with ligroin. The ligroin phase was washed 3 times with water and dried over sodium sulphate. After filtration, the ligroin was distilled off from the filtrate in vacuo and the residue was subjected to incipient distillation under a high vacuum. 32 g (77% of theory) of 3-(2,2-dichlorovinyl)-2,2-dimethyl-cyclopropane-1-carboxylic acid 3- phenoxy-α-cyano-benzyl ester were obtained as the residue.

The following compounds were obtained analogously:

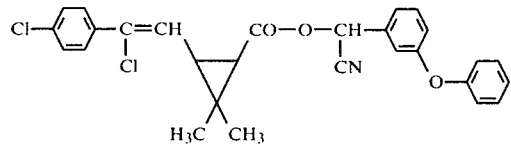

(2)

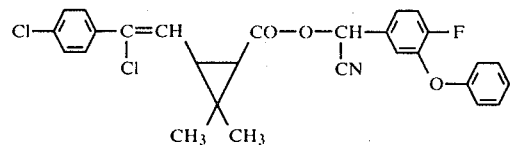

(3)

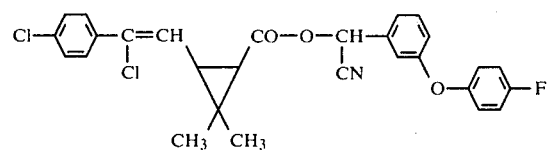

(4)

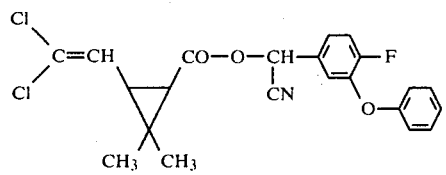

(5)

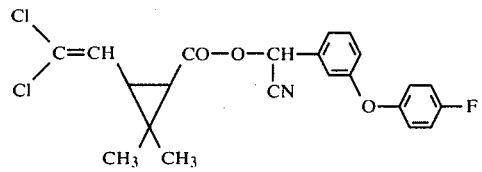

(6)

and

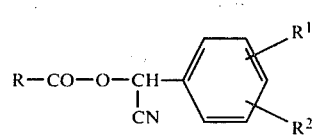

(7)

It will be appreciated that the instant specification and examples are set forth by way of illustration and not limitation, and that various modifications and changes may be made without departing from the spirit and scope of the present invention.

What is claimed is:

1. A process for the preparation of an α-cyano-benzyl ester of the formula

in which

R represents a radical of the formula

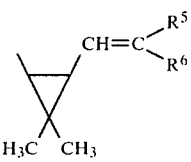

in which
$R^5$ represents hydrogen, methyl, chlorine, or bromine and
$R^6$ represents methyl, chlorine, bromine or optionally halogen-substituted phenyl, or
R represents the radical

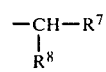

in which
$R^7$ represents phenyl which is optionally substituted by halogen, $C_1$-$C_4$-alkyl, $C_1$-$C_4$-alkoxy, $C_1$-$C_4$-alkylthio, halogenomethyl, $C_1$-$C_2$-halogenoalkoxy, $C_1$-$C_2$-halogenoalkylthio, $C_1$-$C_2$-alkylenedioxy or $C_1$-$C_2$-halogenoalkylenedioxy and
$R^8$ represents isopropyl or cyclopropyl,
$R^1$ represents hydrogen, halogen or an optionally halogen-substituted alkyl, alkenyl, alkynyl, alkoxy, alkenoxy, alkynoxy, aralkyl or aryloxy radical and
$R^2$ represents hydrogen or halogen,
comprising reacting a phosphoric acid α-cyano-benzyl ester of the formula

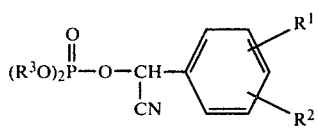

in which
$R^3$ each independently is alkyl or phenyl or both together are alkanediyl,
with a carboxylic acid salt of the formula $$R-CO-O^\ominus M^\oplus$$

in which
M represents one equivalent of an alkali metal or alkaline earth metal,
at a temperature of about 20° to 250° C.

2. A process according to claim 1, in which
$R^1$ represents hydrogen or phenoxy which is optionally substituted by fluorine, chlorine or bromine,
$R^2$ represents hydrogen, fluorine, chlorine or bromine.

3. A process according to claim 1, in which $R^3$ represents 2,2-dimethyl-propane-1,3-diyl.

4. A process according to claim 1, in which M represents lithium, sodium or potassium.

5. A process according to claim 1, in which the reaction is effected in an aprotic dipolar diluent.

6. A process according to claim 5, in which the diluent is selected from ethers, carboxylic acid amides, sulphoxides, sulphones, phosphoric acid amides and nitriles.

7. A process according to claim 1, in which about 0.8 to 1.5 moles of the salt are employed per mole of the phosphoric acid α-cyano-benzyl ester.

8. A process according to claim 2, in which the diluent is selected from ethers, carboxylic acid amides, sulphoxides, sulphones, phosphoric acid amides and nitriles, the reaction is effected at about 100° to 200° C., and about 1.0 to 1.3 moles of the salt are employed per mole of the phosphoric acid α-cyano-benzyl ester.

9. A process according to claim 1, wherein the phosphoric acid α-cyano-benzyl ester is produced by reacting a benzoylphosphonic acid ester of the formula

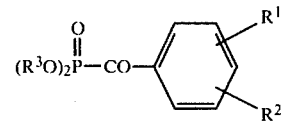

with an alkali metal cyanide in aqueous acetic acid at a temperature from about −20° to +100° C.

* * * * *